United States Patent [19]

Reid et al.

[11] Patent Number: 4,642,292

[45] Date of Patent: Feb. 10, 1987

[54] METHOD FOR ISOLATION OF CONNECTIVE TISSUE BIOMATRIX

[75] Inventors: Lola C. M. Reid, Rye, N.Y.; Marcos Rojkind, Ciudad Satelite, Mexico

[73] Assignee: Albert Einstein College of Medicine of Yeshiva University, a division of Yeshiva University, Bronx, N.Y.

[21] Appl. No.: 499,675

[22] Filed: Jun. 6, 1983

Related U.S. Application Data

[63] Continuation of Ser. No. 307,311, Sep. 30, 1981, abandoned, which is a continuation-in-part of Ser. No. 89,167, Oct. 29, 1979, Pat. No. 4,352,887.

[51] Int. Cl.$^4$ ............................................. C12N 5/00
[52] U.S. Cl. .................................... 435/240; 435/267; 435/273
[58] Field of Search ............... 435/240, 241, 267, 268, 435/270, 271, 272, 273; 260/123.7; 426/429, 430; 435/1; 530/344, 356

[56] References Cited

U.S. PATENT DOCUMENTS

| | | | |
|---|---|---|---|
| 3,660,566 | 5/1972 | Vinson et al. | 435/271 |
| 4,264,155 | 4/1981 | Miyata | 260/123.7 |
| 4,288,557 | 9/1981 | Karkhavis et al. | 435/272 |

OTHER PUBLICATIONS

Meegan et al., Life Sciences, 17(11): 1721–1732.
Reid et al., Methods in Enzymology, vol. LVIII, Academic Press, New York, 263–278 (1979).

Primary Examiner—Esther M. Kepplinger

[57] ABSTRACT

A method is disclosed for isolation of connective tissue fibers, called biomatrix, containing a significant portion of the extracellular matrix, i.e., basement membrane components and components of the ground substance. The connective tissue fibers isolated by this method provide significantly higher survival and attachment rates, and often significantly improved growth properties, for in vitro cultures of differentiated cells, especially epithelial cells, over current culture substrates which do not contain these fibers.

12 Claims, No Drawings

METHOD FOR ISOLATION OF CONNECTIVE TISSUE BIOMATRIX

This is a continuation of application Ser. No. 307,311, filed Sept. 30, 1981 and now abandoned, which was a continuation-in-part of patent application Ser. No. 089,167 filed Oct. 29, 1979 now U.S. Pat. No. 4,352,887 issued Oct. 5, 1982.

FIELD OF THE INVENTION

This invention relates to a method for the isolation of connective tissue fibers, called biomatrix, which are used as a cell culture substrate.

BACKGROUND AND DISCUSSION OF PRIOR ART

Despite numerous advances in cell culture procedures, the culture of differentiated epithelial cells, particularly from normal tissues, has remained especially difficult. It has been proposed that the shortcomings of cell culture techniques are primarily caused by cells being isolated from the extracellular matrix and from association with other cell types with which they may be interdependent. Culture methods, such as organ culture or the culture of tissue fragments, which retain tissues architecture, preserve the differentiative state of the cells, whereas clonal cell cultures usually undergo a dedifferentiative process. Thus, to culture differentiated cells it is necessary to ascertain the critical variables of the tissue matrix and to evolve culture procedures dependent upon them, something the prior art had failed to do.

In the aforementioned patent application, Ser. No. 089,167, now U.S. Pat. No. 4,352,887, connective tissue fibers or biomatrix were disclosed and claimed which, when used as a culture substrate, would simulate some of the cell-cell relationships of the tissue matrix relevant to differentiated cells. On substrates of reconstituted basement membrane and in medium supplemented with hormones, serum, and with conditioned medium from feeder layers of primary cultures of fibroblasts these differentiated cells could be cultured.

The prior art, however, with regard to cell culture substrates and isolation of connective tissue fibers respectively produced either pure collagen (typically of only one type) or produced biomatrix which would be highly toxic to cells if used in culture.

For instance, the reference by Price in *Chemical Abstracts*, entitled "Preparation and use of Rat Tail Collagen" 84: 71179K, 194 (1976) discloses the preparation of a cell culture substrate which comprises only Type I collagen. This is typical of most prior art references for preparation of cell culture substrates. Significantly, the only components of connective tissue-derived fibers studied to date by the prior art have been those which were soluble in one solution or another, because of the prior art's use of a positive selection system (the solubilization of the desired component and subsequent purification of it as an isolated individual entity). The connective tissues-derived fibers isolated by the method claimed herein, however, is a mixture of components, only some of them being collagens. The relevance of this to the differentiative and/or proliferative capacity of cells is due to the synergistic interactions of all these components in their affects on cells. Although cells will respond to one component or another derived from the connective tissue-derived fibers, e.g., collagens, their more normal, physiological response is observed only when they are in contact with the complete connective tissue-derived fibers. Indeed, the collagen fibers isolated by the prior and the other components which make up the "connective tissue fibers", in part but not in toto, have long been known individually to enhance primary cells cultures of differentiated epithelial cells. The complete connective tissue-derived fibers isolated by the disclosed invention, however, have been found to be significantly superior than the individual components alone, since they are comprised of multiple components which are found to synergistically interact on a broader front to enhance cell culturing abilities. All cells are optimally differentiated when they are maintained in vivo. The biomatrix isolated by this invention, when used in culture, provides an in vitro simulation of those in vivo conditions.

The connective tissue-derived fibers also vary in chemical composition from tissue to tissue. Although there are the same types of components (collagens, non-collagenous proteins, and carbohydrates) in all tissues, the specific forms of collagen or other components is different in different tissues. For example:

Skin: Type I collagen predominates. This is typically the type of collagen isolated by the prior art for use in cultures. In association with Type I collagen is an anchorage protein, fibronectin, and proteoglycan, dermatan sulfate. There are other non-collagenous proteins also associated with the Type I collagen but they have not been chemically purified or characterized.

Bone: Type II collagen predominates. In association with Type II collagen is an anchorage protein, chondronectin and proteoglycan, chondroitin sulfate. As above there are other noncollagenous proteins and carbohydrates, undefined, which are found in association with Type II collagen.

Liver: Type IV collagen predominates. In association with Type IV collagen is an anchorage protein, laminin, and proteoglycan, heparan sulfate. Since Type IV collagen is distinguished from the other collagens by its large number of sulfhydryl groups and disulfide bonds, it is in association with many noncollagenous proteins (most of them glycoproteins or proteoglycans) which are bound to the collagen covalently through these sulfur linkages. Indeed, the mixture of specific proteins will be unique to each different type of tissue.

Typically, the prior art references purify the collagen Type I due to its solubility in dilute acids) to various degrees and then either smear it on plates, gel it (non-fibrous; denatured collagen), or reconstitute it into fibers. Purified Type I collagen gels, coats, or fibers have long been used as collagenous substrates for primary cultures of normal epithelial cells. However, not all normal epithelial cells attach to Type I collagen and furthermore the connective tissue-derived fibers isolated by the disclosed invention contains not only Type I collagen but Type II, III and IV and many other components other than collagen. One cannot see the fully normal state of the cells without all of these components. This is because of synergistic interactions between these components and the cultured cells. This synergism is further enhanced by the effect of cell-specific hormones and conditioned medium. One cannot replace the complex composition found in the connective tissue-derived fibers with only one or another of the components present in those fibers.

The prior art has also disclosed the preparation of biomatrix for purposes other than cell culture purposes. See Meezan, et al., entitled "A Simple, Versatile, Nondisruptive Method For The Isolation of Morphologically and Chemically Pure Basement Membranes from Several Tissues", in *Life Sciences,* Vol. 17, pp. 1721–1732. However, because the Meezan end product biomatrix is not being used for cell culture purposes, but merely for chemical analysis purposes, compounds which are toxic to cells in culture are utilized in the isolation and purification steps and are retained by the biomatrix. Specifically, the Meezan process utilizes a sodium azide solution at various steps and residual sodium azide is retained by the biomatrix. Sodium azide has been shown in the prior art to be toxic and mutagenic to mammalian cells in culture. See Seamenova, et al, "The Effects of Sodium Azide on Mammalian Cells Cultivated In Vitro", *Mutation Research,* Volume 71, pp. 253–261 (1980) and Jones, et al., "Toxicity and Mutagenicity of Sodium Azide in Mammalian Cell Cultures," *Mutation Research,* Volume, 77, pp. 293–299 (1980).

Furthermore, the Meezan process also utilizes a deoxycholate solution which also leaves a toxic residue in the end product biomatrix. Another significant distinction is that the Meezan reference does not involve the use of ribonuclease in addition to DNase. The use of ribonuclease and DNase enables the production of more pure connective tissue derived fibers, without any contaminating DNA or RNA, and this is essential for use as a tissue-specific cell culture substrate. The use of DNase in the Meezan article is merely to prevent "viscous gel"-like DNA from interfering with the handling of the biomatrix, but would not result in a similar functional product required when using connective tissue-derived fibers as a culture substrate.

It is therefore an object of this invention to provide a method for the preparation and isolation of a novel and non-toxic cell culture substrate.

It is another object of this invention to provide for the isolation of a biomatrix composition which, when utilized in cell cultures, provides an in vitro simulation of in vivo conditions.

The aforesaid objects as well as other objects and advantages will be made more apparent in reading the following description and the adjoined claims.

DESCRIPTION OF THE PREFERRED EMBODIMENTS

Broadly stated, the present invention relates to a method for preparation and isolation of connective tissue-derived fibers for use in a cell culture comprising:

a. dispersing tissue to form a suspension of connective tissue-derived fibrous solids;

b. separating the connective tissue-derived fibrous solids out of the suspension of step a and adding said solids to a delipidation solution;

c. separating the connective tissue-derived fibrous solids out of the solution of step b and adding said solids to a saline solution containing DNase and Ribonuclease; and d. separating the connective tissue-derived fibrous solids out of the solution of step c and rinsing said solids, first with a saline solution and then with the solution to be used in the culture.

Separation of the solids from the suspension may be by centrifugation or filtration. In addition, the isolated connective tissue-derived fibers may be stored frozen with a cryoprotective agent or sterilized and stored at temperatures above freezing. The delipidation solution may be a detergent, Butanol/ether mixture, or other delipidation solutions.

More specifically, this method comprises:

a. mincing and homogenizing tissue in a volume of water at about 1°–10° C. to form a suspension of connective tissue-derived fibrous solids;

b. separating the connective tissue-derived fibrous solids from the solution of step a;

c. collecting the connective tissue-derived fibrous solids of step b and adding said solids to a quantity of water;

d. blending the mixture of step c for about one hour at about 1°–10° C.;

e. separating the connective tissue-derived fibrous solids from the solution of step d and rinsing the solids with a salt solution;

f. blending the mixture of step e for about one hour at about 1°–10° C.;

g. separating the connective tissue-derived solids from the solution of step f;

h. observing the solution of step g and repeating steps e, f and g until said solution of step g is clear;

i. adding the connective tissue-derived solids of step g to an amount of serum-free medium equal to about half the amount of tissue used in step a;

j. adding DNase and ribonuclease to the serum-free medium of step i at a ratio of about 1 mg: 50 ml and 5 mg: 50 Ml, respectively;

k. blending the mixture of step j for about 1 hour at about 30°–45° C.;

l. separating the connective tissue-derived fibrous solids from the solution of step k and staining a sample of said solids with nucleic acid stain;

m. repeating steps i, j, k and l until said sample stain indicates nucleic acids are removed;

n. rinsing the connective tissue-derived fibrous solids of step l in a salt solution for at least about 0.5 hour;

o. separating the connective tissue-derived fibrous solids from the solution of step n and adding said solids to a delipidation solution;

p. stirring the mixture of step o for about one hour;

q. separating the connective tissue-derived fibrous solids from the solution of step p and washing them with water at least about one time;

r. adding the connective tissue-derived fibrous solids of step q to serum-free medium, keeping said mixture at about 1°–10° C. while stirring said mixture for about 12 hours; and s. separating the connective tissue-derived fibrous solids from solution of step r whereby the solids are connective tissue-derived fibers ready to use in cultures as a culture substrate.

Preferably, this method comprises:

a. mincing tissue and homogenizing by hand or in a Waring blender, using 5–10 vol of cold distilled water per gram of tissue, while keeping sample at about 4° C. to form a suspension of connective tissue-derived fibrous solids. The preferable amount of starting material is about 100 grams;

b. immediately filtering through a filter, preferably polyester, into a 2- to 4-liter beaker placed in ice;

c. collecting connective tissue-derived fibrous solid filtrate on top of the polyester filter and putting said filtrate into a beaker with water, then washing polyester filter thoroughly and adding the wash to the beaker;

d. stirring the solution of step c for about 1 hour at about 4° C.;

e. filtering the solution of step d through polyester and then repeating step c, using 0.1–1.0M NaCl;

f. stirring the solution of step f for about 1 hour at about 4° C.;

g. collecting the connective tissue-derived fibrous/solid precipitate from the solution of step f by filtration through the polyester filter. If the solution is very opaque, repeat steps e–g until the solution is clear;

h. putting the connective tissue-derived fibrous solid precipitate retained on the filter into a small amount of serum-free medium (about 30–50 ml/100 g of starting material) and add about 1.0 mg of DNase and about 5 mg of ribonuclease per 50 ml of serum-free medium;

i. stir the solution of step h for about 1 hour at about 37° C.;

j. stirring a sample of the connective tissue-derived fibrous solid precipitate of step i with Acridine Orange (0.3% in distilled water). The nucleic acid contaminants stain an intense orange with this solution. Precipitate reasonably free of these contaminants will stain a pale salmon color. Repeating steps h–j until the precipitate is clean of nucleic acid components;

k. collecting connective tissue-derived fibrous solid precipitate of step j by filtration and rinsing said precipitate in 0.1–1.0M NaCl or in serum-free medium for about 0.5 h;

l. collecting connective tissue-derived fibrous solid precipitate of step k by filtration and add to 100 ml of of distilled water over which is layered an equal volume of about a 40:60 Butanol/ether solution. The mixture is then stirred about every 5 min for 0.5–1 hour at about room temperature;

m. sampling the connective tissue-derived fibrous solid precipitate of step l and adding to an oil red O solution. If translucent red globules are present, repeat step l and m until they disappear. The translucent red material would appear within 3–5 min.;

n. collecting the connective tissue-derived fibrous solid precipitate by filtration and wash with 250 ml of distilled water at least about three times (about 1 hour each), separating connective tissue-derived fibrous solids from solution between washings;

o. stirring the connective tissue-derived fibrous solid precipitate overnight in PBS or serum-free medium (1×10 volume) at about 4° C.; and p. collecting the connective tissue-derived fibrous solid precipitate connective tissue-derived fibers by filtration and either using immediately for culture or chemical studies or store by freezing at −20° C. in serum-free medium plus 10% glycerol.

Oil red O used in the procedure above, comprises 0.5% in 60% isopropanol (stock solution). For use, dilute 6 parts stock to 4 parts water, mix on a vortex, and filter.

The invention disclosed herein is further illustrated by the following experiment.

EXPERIMENT I

This invention and experiment relates to the isolation of connective tissue fibers, called biomatrix, containing a significant portion of the extracellular matrix (basement membrane components and components of the ground substance). Biomatrix isolated from normal rat liver contains more than 90% of the tissue's collagens and all of the known collagen types, including types I and III and basement membrane collagens. The purified collagenous fibers are associated with noncollagenous acidic proteins (including fibronectins and possibly small amounts of glycosaminoglycan). Procedures are also described for preparing tissue culture substrates with these fibers by either smearing tissue culture dishes with frozen sections or by shredding the biomatrix into small fibrils with a homogenizer. The biomatrix as a substrate has a remarkable ability to sustain normal rat hepatocytes long-term in culture. The hepatocytes, which on tissue culture plastic or on type I collagen gels do not survive more than a few weeks, have been maintained for more than 5 months in vitro when cultured on biomatrix. These cells cultured on rat liver biomatrix show increased attachment and survival efficiencies, long-term survival (months), and retention of some hepatocyte-specific functions. This experiment is also outlined in the article by M. Rojkind, et al., entitled "Connective Tissue Biomatrix: Its Isolation and Utilization for Long-term Cultures of Normal Rat Hepatocytes", *The Journal of Cell Biology*, 87:255–263 (1980).

MATERIALS AND METHODS

Animals

Adult Sprague-Dawley rats were purchased from Charles River Breeding Laboratories, Wilmington, Mass., and used immediately for purification of type I collagen and/or biomatrix.

Preparation of Isolated Rat Hepatocytes

Suspensions of isolated rat hepatocytes were prepared. The cells were washed free of bacterial collagenase with culture medium, diluted, and counted. Cell viability was determined by trypan blue exclusion.

Culture Conditions

Media and solutions: The cells were cultured in minimum essential medium (MEM) or a 1:1 mixture of Dulbecco's modified Eagle's medium (DME) and Ham's F12 supplemented with trace elements, HEPES, and with 10% fetal bovine serum (FBS). The medium is referred to as DME/F12+FBS. All supplies for medium were obtained from Grand Island Biological Co., Grand Island, N.Y. The trace elements were a gift from R. Ham (University of Colorado, Boulder, Colo.). Dulbecco's phosphate-buffered saline (PBS) without magnesium or calcium salts was prepared from reagent grade chemicals from Baker.

Plastic: All tissue culture plastics were obtained from Falcon Labware.

Substrates: The cells were grown on one of three possible substrates: tissue culture dishes, collagen gels, or rat liver biomatrix. Preparation of the latter two is described below.

Preparation of Rat Liver Biomatrix

After decapitation of a rat, the liver was homogenized gently in a loose-fitting glass teflon homogenizer, using 10 vol. of ice-cold distilled water, and immediately passed through a polyester filter (PeCap HD7-85, from TETKTO, Inc., Elmsford, N.Y.) of 166–168 mesh per inch. The material retained on the polyester was collected with a spatula and then purified as described above. Triplicate aliquots of all filtrates and final retentate were hydrolyzed in 6N HCl for 24 hours at 104° C. and analyzed for hydroxyproline content. Collagen was estimated from the amount of hydroxyproline, assuming that each polypeptide chain of 100,000 daltons contains 1,000 residues.

MORPHOLOGICAL Characterization of the Rat Liver Biomatrix

Rat liver biomatrix obtained at different stages of purification was fixed in 2% glutaraldehyde in phosphate buffer, dehydrated with an ethanol series, embedded in Epon, and sectioned for electron microscopy. Freshly prepared fibers were also fixed in buffered formaldehyde, dehydrated with an ethanol series, embedded in paraffin, and sectioned at 5 $\mu$m. These sections were stained for reticulin fibers.

After the final stages of purification, rat liver biomatrix was stained in whole mount preparations with ruthenium red or by period acid-Schiff (PAS) staining. Fibronectin analysis was determined by indirect immunofluorescence. Frozen sections, 8 $\mu$m each of collagen gels or of biomatrix with or without cells attached, were fixed in 2% paraformaldehyde in 0.1M PBS and stained with rabbit antichicken fibronectin. The sections were secondarily stained with fluorescein-labeled antirabbit antiserum. The fibronectin used as antigen was purified from embryo fibroblast cell cultures. The stained slides were evaluated with a Zeiss fluorescence microscope. Control slides were stained with rabbit serum from nonimmunized rabbits.

Collagenase Digest of Purified Rat Liver Biomatrix

Biomatrix (30-50 mg of wet weight) was incubated for 24 hours at 20° C. with 1 ml. of 0.05M Tris-HCl buffer, pH F4, with 0.005M $CaCl_2$, containing 20 $\mu$g of bacterial collagenase (412 U/mg), Bacterial collagenase was freed of nonspecific protease activity. After incubation, the fibers were centrifuged at 3,000 r.p.m. for 30 min and the supernatant was transferred to a vial and evaporated to dryness. 1 ml of constant boiling HCl was added, and the sample was sealed under vacuum. The residue after collagenase digestion was transferred to a second vial and also prepared for acid hydrolysis. Samples were treated at 104° C. for 24 hours and used for aminoacid analysis. Corrections were made for recovery of amino acids using norleucin as a standard. No corrections were made for losses after acid hydrolysis. The amount of collagen was estimated from the hydroxyproline content of the sample as described above. The noncollagenous proteins were estimated from the amino composition of the sample.

Analytical Methods

About 300 mg. of liver was used for acid hydrolysis and hydroxyproline determination. For carbohydrate analysis, samples of fibers of 20-30 mg. of wet weight were hydrolyzed for 3 hours at 104° C. with 2 ml of 2N HCl. Excess HCl was evaporated to dryness in a flash evaporator, and the sample was dissolved in 2 ml of distilled water. Aliquots (0.5-1.0 ml) were used for hexose analysis with anthrone. Glucose was used as a standard, and the results are expressed as glucose equivalents per milligram of biomatrix. Protein determinations were also done.

Uronic acid determination was performed on 1 gram of fresh liver or 100 mg of biomatrix by a modification of the carbazole reaction. Liver or biomatrix was first incubated for 24 hours at 4° C. with 1N NaOH, neutralized with 0.1N HCl, and digested for 24 hours with pronase. Protein was precipitated with TCA (final concentration of 10%) and removed by centrifugation. The supernatant was dialyzed exhaustively against distilled water, aliquots were used for uronic acid determination. Qualitative determination of the presence of glycoproteins and glycosaminoglycans was done with ruthenium red staining.

Preparation of Cell Culture Substrates

Collagen Gel Rafts: Collagen gel rafts were prepared as described in the article entitled, "New Techniques for Culturing Differentiated Cells: Reconstituted Basement Membrane Rafts." in *Methods Enzymol.* 58: 263-278 by Reid, et al.

Biomatrix: Prepared according to the procedure claimed herein. To make culture substrates, the best results were obtained by embedding the biomatrix into polyvinyl pyrrolidone, Tissue Tec, manufactured by Miles Scientific a division of Miles Laboratories Inc. of Naperville, Ill., and freezing it at $-20°$ C. 5- to 10-$\mu$m sections were cut on a cryostat and smeared over tissue culture plates with small camel hair brushes. The plates was used were thoroughly rinsed with 3 to 4 changes of PBS and soaked overnight with serum-free medium before use for culture experiments. An alternative to the above was to homogenize the biomatrix with a polytron homogenizer until it was shredded into short fibrils of 1-3 mm of length. The homogenization was done in PBS or serum-free medium maintained at 4° C. and with 10- to 15-second bursts of the homogenizer. Cells were attached to the fibrils and either allowed to sit on the bottom of the dish or kept in suspension by the use of a sterilized magnetic stirrer. With this method the cells do not have to be detached in order to subculture the plate. A portion of the fibrils with attached cells can be transferred to a new dish with more fibrils.

Sterilization of the biomatrix fibrils or of the plates smeared with biomatrix was done by irradiation with 10,000 rads of cobalt gamma radiation. Although sterilization of the substrates could also be effected by 5,000 rads of gamma irradiation or by UV irradiation, the sterilization procedures were occasionally inadequate for control of mold spores. Therefore, the high-dosage gamma irradiation was adopted exclusively.

Evaluation of the Cultures

Morphologic Studies: Suspensions of isolated rat hepatocytes were added to either tissue culture dishes, type-I collagen gel rafts or rat liver biomatrix. Cultures were maintained for up to 5-6 months, with the media being changed once weekly. Photographs were taken at regular intervals with a Nikon inverted phase microscope. For histological studies, cell cultures were fixed in methanol or with buffered formaldehyde, dehydrated, and embedded in paraffin. 8-$\mu$m sections were stained with hematoxylin/eosin.

Attachment Efficiency: Suspensions of rat hepatocytes at varying densities were plated onto one of three substrates. The cultures were provided with a medium of MEM or DME/F12+FBS and incubated at 37° C. in an incubator flushed with 95% air and 5% $CO_2$. The cultures were maintained for 2 hours after which the plates were rinsed twice with PBS, and the attached cells were removed with 0.1% collagenase in serum-free medium. The number of viable cells was counted and analyzed by trypan blue exclusion.

Long-term Survival Efficiencies and the Duration of the Cultures

Varying densities of rat hepatocytes were added to 35- or 60-mm dishes with one of the possible substrates. The cultures were provided with a medium or MEM or DME/F12+FBS and incubated at 37° C. in an incubator flushed with 95% air and 5% $CO_2$. The cultures were maintained for 3-4 weeks after which the plates were rinsed and the attached cells were removed with 0.1% collagenase in serum-free medium. The number of viable cells was counted and analyzed by trypan blue exclusion. The potential duration of the cultures was estimated by plating $10^5$-$10^6$ cells on one of the various substrates in 35- to 60-mm dishes and maintaining the cultures with weekly changes of medium for as long as the cells seemed viable. If the cultures seemed to be dying, the experiment was terminated and the cells detached by enzymatic treatment and evaluated for viability.

Differentiated Functions

Qualitative studies using indirect immunofluorescence have shown that cells contained albumin and ligandin for as long as the cultures were maintained. In Table IV are presented the qualitative data on cultures maintained for more than 3 mo. Albumin synthesis was confirmed on day-15 cultures by incubating them with labeled amino acids, homogenizing the cells, and running them on SDS gels. Fluorography of the radioactivity in the area of the albumin standard band indicated the presence of newly synthesized albumin material. Quantitative studies of bilirubin conjugation and of the presence of other hepatocyte-specific markers have been submitted elsewhere in the prior art. In brief, the cells after 6-8 wk on biomatrix contained all reactions involved in bilirubin production and conjugation. They were positive for glutathione-S-transferase, glutamic pyruvic transaminase (GPT), and glutamic oxaloacetic transaminase (GOT), and for the ability to metabolize azodye carcinogens.

Discussion

With this invention, one can isolate a portion of the extracellular matrix and use it as a substrate for long-term cultures of normal rat hepatocytes. The use of individual components of the extracellular matrix for culturing cells has long existed. Investigators have used plates coated with collagen in a variety of forms, more recently, fibronectins for primary cultures of differentiated epithelial cells. The innovation described is the use of a substrate that is a complex mixture of some of the components known to be in the extracellular matrix. The method of isolation reflects the realization of a need for multiple components. The method involves a series of solubilizations to eliminate undesired components and repeated selection for unsolubilized fibers longer than 80 μm. The solubilizations eliminate DNA, RNA, lipids, and components solubilized in water or low-ionic-strength salt buffers. The advantages are that the procedures select for native collagen fibers and their associated non-collagenous proteins and carbohydrates, components known to be in basement membranes. As indicated in Tables I and II, the biomatrix isolated from rat liver is composed of all the known liver collagens, some glycoproteins including fibronectins, and possible some glycosaminoglycans. Further characterization of the noncollagenous proteins and of the possible presence of glycosaminoglycans is currently under way. More extensive characterization of the collagenous components has been presented elsewhere in the prior art.

Use of the biomatrix as a cell culture substrate indicates that it is substantially better than other substrates currently in use for hepatocytes. The attachment and survival efficiencies as indicated in Table III are dramatically improved. The potential lifespan of the cultures using biomatrix is not known. Some cultures have been maintained for more than 5 months. The presence of viable and functional hepatocytes has been confirmed by qualitative evaluations of the presence of ligandin and albumin (Table IV).

Whether or not the hepatocytes can grow on biomatrix is unknown, because the investigations into the growth of the cultures are incomplete and inconclusive. In related studies, however, differentiated prostatic tumor cells and Syrian hamster insulinoma cells did grow on biomatrix. Thus, it seems that growth of some cell types is feasible under these new substrate conditions.

In the specification herein, there have been set forth preferred embodiments of the invention, and although specific terms are employed, they are used in a generic and descriptive sense only and not for purposes of limitation.

In as much as many changes could be made in the above invention, and many apparently different embodiments of the invention could be made without departing from the scope thereof, it is intended that all matters contained in the above description shall be interpreted as illustrative and not in a limiting sense.

TABLE I

Amino Acid Composition of Collagenase-soluble and Collagenase-resistant Proteins of the Liver*

| Amino acid | Collagenase soluble | Collagenase resistant |
|---|---|---|
| | Residues/1,000 amino acid residues | |
| 4-Hydroxyproline | 78 | 0 |
| Aspartic Acid | 57 | 117 |
| Threonine | 23 | 44 |
| Serine | 19 | 31 |
| Glutamic Acid | 71 | 117 |
| Proline | 96 | 57 |
| Glycine | 301 | 131 |
| Alanine | 102 | 78 |
| ½ Cystine | trace | 31 |
| Valine | 41 | 68 |
| Methionine | 7 | 7 |
| Isoleucine | 26 | 57 |
| Leucine | 41 | 71 |
| Tyrosine | 3 | 13 |
| Phenylalanine | 22 | 42 |
| Hydroxylysine | 10 | 0 |
| Lysine | 46 | 77 |
| Histidine | 14 | 21 |
| Arginine | 43 | 38 |

*Average of two preparations.
Not corrected for losses after acid hydrolysis.
Determined as methionine and methionine sulfoxides.

TABLE II

Composition of the Biomatrix Derived from Rat Liver

| | Collagens (mg/100 mg protein) | Types of collagen (% of total collagen) | Noncollagenous proteins (mg/100 mg protein) | Carbohydrates (μmol glucose equiv./100 mg protein) |
|---|---|---|---|---|
| Prep I | 63.7 | Type I, 43% Type III, 42.7% Basement | 36.2 | 9.0 |

TABLE II-continued

Composition of the Biomatrix Derived from Rat Liver

| | Collagens (mg/100 mg protein) | Types of collagen (% of total collagen) | Noncollagenous proteins (mg/100 mg protein) | Carbohydrates ($\mu$mol glucose equiv./100 mg protein) |
|---|---|---|---|---|
| | | membrane collagens (A + B), 6.2% *Undefined, 10.9% | | |
| Prep II | 60.9 | As above | 39.1 | 10.0 |

Proportion of the liver recoverable as biomatrix (given as [amount in biomatrix-]/[amount in liver] × 100 = %): Wet wt (g), 1.14%: the yield of biomatrix by weight is the average of 50 normal rat livers. Total collagen (mg), 95%; the % yield of collagen in the biomatrix is the average of 5 normal rat livers. Total protein (mg), 0.87%: noncollagenous proteins (mg), 0.35%: the % yield of total protein and noncollagenous proteins is the average of two normal rat livers.
*Undefined represents a mixture of type-IV collagen and other minor components not yet characterized.

TABLE III

Attachment and Survival Properties of Rat Hepatocytes on Various Substrates

| | | Substrates | | |
|---|---|---|---|---|
| Property | Seeding density | Plastic % | Collagen gels % | Biomatrix % |
| Attachment efficiency | $10^4$ | 25 | 30 | 85 |
| | $10^5$ | 30 | 45 | 77 |
| | $10^6$ | 55 | 70 | 10 |
| Survival efficiency of the attached cells at 3 wk | $10^4$ | 0 | ≅50* | >95 |
| | $10^5$ | 0 | ≅50 | >95 |
| | $10^6$ | 0 | ≅50 | >95 |
| Duration of the cultures | $10^4$–$10^6$ | 1–2 wk | 4–5 wk | >5 mo |

*The % of viable cells on collagen gels was quite variable, ranging from 35 to 60%. On the average, −50% of the cells were still alive after 3 wk.

TABLE IV

Ligandin and Albumin Markers in Rat Hepatocytes Cultured on Biomatrix

| Conditions | Ligandin* | Albumin |
|---|---|---|
| Whole liver (in vivo) | + | + |
| Freshly isolated hepatocytes | + | + |
| Hepatocytes cultured on rat liver biomatrix | | |
| 5 d | + | + |
| 15 d | + | + |
| 30 d | + | + |
| 60 d | + | + |
| 100 d | + | + |

*Evaluated by indirect immunofluorescence as described in Materials and Methods. Albumin synthesis confirmed as described in Materials and Methods.

What is claimed is:

1. A method for the preparation, isolation and use of connective tissue-derived fibers as a substrate in a cell culture of viable and functional differentiated cells comprising the steps of:
   a. dispersing tissue to form a suspension of connective tissue-derived fibrous solids;
   b. separating the connective tissue-derived fibrous solids out of the suspension of step a and adding said solids to a delipidation solution;
   c. separating the connective tissue-derived fibrous solids out of the solution of step b and adding said solids to a saline solution containing DNase and Ribonuclease;
   d. separating the connective tissue-derived fibrous solids out of the solution of step c;
   e. rinsing said connective tissue-derived fibrous solids, first with a saline solution and then with the solution to be used in the cell culture; and
   f. utilizing the connective tissue-derived fibrous solids of step e as a substrate in a cell culture of viable and functional differentiated cells.

2. The method of claim 1, wherein the separating of the solution components is by filtration.

3. The method of claim 1, wherein the separating of the solution components is by centrifugation.

4. The method of claim 1, wherein the connective tissue-derived fibrous solids of step e are stored frozen in a saline solution with a cryoprotective agent.

5. The method of claim 1, wherein the connective tissue-derived fibrous solids of step e are sterilized and then stored at temperatures above freezing.

6. The method of claim 1, wherein the saline solution is 0.1–1.0M NaCl.

7. The method of claim 1, wherein the solution to be used in the cell culture of step e is a serum-free medium.

8. The method of claim 1, wherein the delipidation solution of step b is about a 40:60 Butanol/ether solution.

9. A method for the preparation, isolation and use of connective tissue-derived fibers containing a significant portion of the extracellular matrix and a plurality of collagen types, for use as a substrate in a cell culture of viable and functional differentiated cells, comprising the steps of:
   a. dispersing tissue to form a suspension of connective tissue-derived fibrous solids;
   b. separating the connective tissue-derived fibrous solids out of the suspension of step a and adding said solids to a delipidation solution selected from the group consisting of a detergent and a Butanol/ether mixture;
   c. separating the connective tissue-derived fibrous solids out of the solution of step b and adding said solids to a saline solution containing DNase and Ribonuclease at a ratio of addition of about 1 mg of DNase and about 5 mg of Ribonuclease per fifty ml of serum-free medium;
   d. separating the connective tissue-derived fibrous solids out of the solution of step c;
   e. rinsing said solids, first with saline solution, and then with the solution to be used in the cell culture; and
   f. utilizing the solids of step e as a substrate in a cell culture of viable and functional differentiated cells.

10. The method of claim 9 wherein, the differentiated cells are epithelial cells.

11. The method of claim 9 wherein, the differentiated cells are hepatocytes.

12. The method of claim 9 wherein, the extracellular matrix comprises basement membrane components and components of the ground substance.

* * * * *